(12) United States Patent
Dale et al.

(10) Patent No.: US 9,775,877 B2
(45) Date of Patent: Oct. 3, 2017

(54) COMBINATIONS WITH A BACKBONE-CYCLIZED PEPTIDE

(71) Applicant: POLYPHOR AG, Allschwil (CH)

(72) Inventors: Glenn E. Dale, Basel (CH); Daniel Obrecht, Bättwil (CH); Francesca Bernardini, Hésingue (FR)

(73) Assignee: POLYPHOR AG, Allschwil (CH)

( * ) Notice: Subject to any disclaimer, the term of this patent is extended or adjusted under 35 U.S.C. 154(b) by 0 days.

(21) Appl. No.: 14/419,986

(22) PCT Filed: Aug. 7, 2013

(86) PCT No.: PCT/EP2013/066530
§ 371 (c)(1),
(2) Date: Feb. 6, 2015

(87) PCT Pub. No.: WO2014/023757
PCT Pub. Date: Feb. 13, 2014

(65) Prior Publication Data
US 2015/0216927 A1      Aug. 6, 2015

(30) Foreign Application Priority Data

Aug. 8, 2012   (EP) .................................... 12005744

(51) Int. Cl.
| | |
|---|---|
| *A61K 38/12* | (2006.01) |
| *A61K 38/10* | (2006.01) |
| *C07K 7/08* | (2006.01) |
| *C07K 7/64* | (2006.01) |
| *A61K 31/65* | (2006.01) |
| *C07K 7/50* | (2006.01) |
| *A61K 47/48* | (2006.01) |

(52) U.S. Cl.
CPC ............... *A61K 38/12* (2013.01); *A61K 31/65* (2013.01); *A61K 38/10* (2013.01); *C07K 7/08* (2013.01); *C07K 7/64* (2013.01); *A61K 47/48407* (2013.01); *A61L 2300/406* (2013.01); *C07K 7/50* (2013.01)

(58) Field of Classification Search
None
See application file for complete search history.

(56) References Cited

FOREIGN PATENT DOCUMENTS

| | | | | |
|---|---|---|---|---|
| CH | WO2007079605 A2 * | 7/2007 | ............... | C07K 7/06 |
| WO | WO2010017273 A2 * | 2/2010 | ............. | A61K 47/26 |

OTHER PUBLICATIONS

Baldwin et al., "Meropenem: A Review of its Use in the Treatment of Serious Bacterial Infections", Drugs, vol. 68, No. 6, 2008, pp. 803-838.
Bonfiglio et al., "Recent Developments in Carbapenems", Expert Opinion Investig. Drugs, vol. 11, No. 4, 2002, pp. 529-544.

* cited by examiner

*Primary Examiner* — Satyanarayana R Gudibande
*Assistant Examiner* — Jia-Hai Lee
(74) *Attorney, Agent, or Firm* — Birch, Stewart, Kolasch & Birch, LLP

(57) ABSTRACT

A novel combination comprising a β-hairpin peptidomimetic of the formula cyclo(-Thr-Trp-Ile-Dab-Orn-$^D$Dab-Dab-Trp-Dab-Dab-Ala-Ser-$^D$Pro-Pro) (I), and a compound of the glycylcycline class, especially tigecycline, that enable therapeutic control of specific bacterial infections in human or animals at doses of the individual compounds lower than either of the compounds administered alone. The combination can be used as a medicament to treat e.g. skin or soft tissue infections; eye, ear, blood stream, or intra-abdominal infections; infections related to respiratory diseases, to bone diseases, to cardiovascular diseases, to genitourinal diseases, or to gastrointestinal diseases.

10 Claims, No Drawings

```
                               SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: synthetic construct
<220> FEATURE:
<221> NAME/KEY: MISC_FEATURE
<222> LOCATION: (4)..(4)
<223> OTHER INFORMATION: Dab
<220> FEATURE:
<221> NAME/KEY: MISC_FEATURE
<222> LOCATION: (5)..(5)
<223> OTHER INFORMATION: Orn
<220> FEATURE:
<221> NAME/KEY: MISC_FEATURE
<222> LOCATION: (6)..(6)
<223> OTHER INFORMATION: DDab
<220> FEATURE:
<221> NAME/KEY: MISC_FEATURE
<222> LOCATION: (7)..(7)
<223> OTHER INFORMATION: Dab
<220> FEATURE:
<221> NAME/KEY: MISC_FEATURE
<222> LOCATION: (9)..(9)
<223> OTHER INFORMATION: Dab
<220> FEATURE:
<221> NAME/KEY: MISC_FEATURE
<222> LOCATION: (10)..(10)
<223> OTHER INFORMATION: Dab
<220> FEATURE:
<221> NAME/KEY: MISC_FEATURE
<222> LOCATION: (13)..(13)
<223> OTHER INFORMATION: DPro
```

```
<400> SEQUENCE: 1

Thr Trp Ile Xaa Xaa Xaa Xaa Trp Xaa Xaa Ala Ser Xaa Pro
1               5                   10
```

COMBINATIONS WITH A BACKBONE-CYCLIZED PEPTIDE

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "24655 ST25.txt" created on Dec. 2, 2015, and is 889 bytes in size. The sequence listing contained in this .txt file is part of the specification and is herein incorporated by reference in its entirety.

The present invention provides a combination of compounds that enable therapeutic control of specific bacterial infections in human or animals at doses of the individual compounds lower than either of the compounds administered alone. One of the compounds is a pathogen-specific antibiotic backbone-cyclized peptide incorporating a chain of 12 α-amino acid residues attached to a template which provides specific structural constraints for a β-hairpin-like conformation showing high efficacy and bio-availability, and remarkably long half-life in vivo.

The growing problem of microbial resistance to established antibiotics has stimulated intense interest in developing novel antimicrobial agents with new modes of action (H. Breithaupt, *Nat. Biotechnol.* 1999, 17, 1165-1169). One emerging class of antibiotics is based on naturally occurring cationic peptides (T. Ganz, R. I. Lehrer, *Mol. Medicine Today* 1999, 5, 292-297; R. M. Epand, H. J. Vogel, *Biochim. Biophys. Acta* 1999, 1462, 11-28). These include disulfide-bridged β-hairpin and β-sheet peptides (such as the protegrins [0. V. Shamova, H. A. Korneva, R. I. Lehrer, *FEBS Lett.* 1993, 327, 231-236], tachyplesins [T. Nakamura, H. Furunaka, T. Miyata, F. Tokunaga, T. Muta, S. Iwanaga, M. Niwa, T. Takao, Y. Shimonishi, Y. *J. Biol. Chem.* 1988, 263, 16709-16713], and the defensins [R. I. Lehrer, A. K. Lichtenstein, T. Ganz, *Annu. Rev. Immunol.* 1993, 11, 105-128], amphipathic α-helical peptides (e.g. cecropins, dermaseptins, magainins, and mellitins [A. Tossi, L. Sandri, A. Giangaspero, *Biopolymers* 2000, 55, 4-30]), as well as other linear and loop-structured peptides. Although the mechanisms of action of antimicrobial cationic peptides are not yet fully understood, their primary site of interaction is the microbial cell membrane (H. W. Huang, *Biochemistry* 2000, 39, 8347-8352). Upon exposure to these agents, the cell membrane undergoes permeabilization, which is followed by rapid cell death. However, more complex mechanisms of action, for example, involving receptor-mediated signaling, cannot be ruled out (M. Wu, E. Maier, R. Benz, R. E. Hancock, *Biochemistry* 1999, 38, 7235-7242; M. Scocchi, A. Tossi, R. Gennaro, *Cell. Mol. Sci.* 2011, 68, 2317-2330).

The antimicrobial activities of many of these cationic peptides usually correlate with their preferred secondary structures, observed either in aqueous solution or in membrane-like environments (N. Sitaram, R. Nagaraj, *Biochim. Biophys. Acta* 1999, 1462, 29-54). Structural studies by nuclear magnetic resonance (NMR) spectroscopy have shown that cationic peptides such as protegrin 1 (A. Aumelas, M. Mangoni, C. Roumestand, L. Chiche, E. Despaux, G. Grassy, B. Calas, A. Chavanieu, A. *Eur. J. Biochem.* 1996, 237, 575-583; R. L. Fahrner, T. Dieckmann, S. S. L. Harwig, R. I. Lehrer, D. Eisenberg, J. Feigon, *J. Chem. Biol.* 1996, 3, 543-550) and tachyplesin I (K. Kawano, T. Yoneya, T. Miyata, K. Yoshikawa, F. Tokunaga, Y. Terada, S. J. Iwanaga, S. *J. Biol. Chem.* 1990, 265, 15365-15367) adopt well defined β-hairpin conformations, due to the constraining effect of two disulfide bridges. However, the high hemolytic activity hindered their widespread use as antibiotics. Recent structural studies by NMR have indicated that the high hemolytic activity apparently correlates with the highly amphipathic nature of this cyclic β-hairpin-like molecule, but that it is possible to dissociate antimicrobial and hemolytic activities by modulating the conformation and amphiphilicity (L. H. Kondejewski, M. Jelokhani-Niaraki, S. W. Farmer, B. Lix, M. Kay, B. D. Sykes, R. E. Hancock, R. S. Hodges, *J. Biol. Chem.* 1999, 274, 13181-13192; C. McInnesL. H. Kondejewski, R. S. Hodges, B. D. Sykes, *J. Biol. Chem.* 2000, 275, 14287-14294).

Recently a series of antibiotic compounds following these design criteria are disclosed in WO2007079605, respectively WO2007079597, which combine a high efficacy specifically against *Pseudomonas aeruginosa* with low hemotoxic effects. This series is following earlier disclosures introducing these concepts in WO2002070547 and WO2004018503. With the compounds described therein, a new strategy was introduced to stabilize β-hairpin conformations in backbone-cyclic cationic peptide mimetics exhibiting the selective high antimicrobial activity. This involved transplanting the cationic and hydrophobic hairpin sequence onto a template, whose function is to restrain the peptide loop backbone into a hairpin geometry.

Template-bound hairpin mimetic peptides of this type have been also described in the literature (D. Obrecht, M. Altorfer, J. A. Robinson, *Adv. Med. Chem.* 1999, 4, 1-68; J. A. Robinson, *Syn. Lett.* 2000, 4, 429-441) and the ability to generate β-hairpin peptidomimetics using combinatorial and parallel synthesis methods has been established (L. Jiang, K. Moehle, B. Dhanapal, D. Obrecht, J. A. Robinson, *Helv. Chim. Acta.* 2000, 83, 3097-3112).

An alternative approach to counteract the increasing prevalence and spread of multidrug-resistant bacteria is to modify and further develop antibiotic substances from commonly used classes. A prominent achievement was in recent years the development of tigecycline, creating a new class of highly potent antibiotics termed the glycylcyclines. This class of novel expanded spectrum antibiotics has revealed in in vitro testing high microbiological activity against aerobic to anaerobic, Gram-positive and Gram-negative bacteria, as well as atypical organisms, but is especially important against vancomycin-resistant enterococci, methicillin-resistant *Staphylococcus aureus*, penicillin-resistant *Streptococcus pneumoniae* and many species of multidrug-resistant Gram-negative bacteria (review: G. A. Pankey, *J. Antimicrob. Chemother.*, 2005, 56, 470-480). In vivo studies and clinical trials could confirm the high efficacy and established a favourable safety profile for a series of indications for which market authorisation is currently granted (reviews: Y. Cai, R. Wang, B. Liang, N. Bai, Y. Liu, *Antimicrob. Agents Chemother.*, 2011, 55, 1162-1172; D. Yahav, A. Lador, M. Paul, L. Leibovici, *J. Antimicrob. Chemother.*, 2011, 66, 1963-1971; E. Tasina, A. B. Haidich, S. Kokkali, M. Arvanitidou, *Lancet Infect. Dis.*, 2011, 11, 834-844).

Still, the therapeutic use of tigecycline as a broad-spectrum antibiotic is far from perfect, leaving loopholes for low responsive pathogens, such as e.g. *Pseudomonas aeruginosa*. Tigecycline is as well of limited use for certain nosocomial infections, e.g. hospital-acquired pneumonia due to an unfavourable risk-benefit ratio.

Therefore an extension of the therapeutic window of tigecycline, as a representative of the glycylcycline class of antibiotics, would be extremely beneficial.

This could in one way be achieved by treatment options extending the efficacy to bacteria having high susceptibility breakpoints for tigecycline or to be able to lower the effective amount of the therapeutic drug in clinical cases judged so far as associated with an unfavourable risk-benefit ratio. The standard approach in a clinical setting to avoid the shortcoming of a tigecycline monotherapy is to combine the drug with complementary antibiotics.

Historically different methodologies were employed to characterize the biological effect of two pharmaceutically active ingredients separate and in combination (E. Jawetz, *Antimicrob. Agents Chemother.*, 1967; 203-209; T.-C. Chou, P. Talalay, *Adv. Enzyme Regul.*, 1984, 22, 27-55). Meanwhile a broad consent is reached about the classification of observed drug-drug interaction, especially for antibiotics. According to this terminology basically depending on the quantity of the combined dose-response effect the drug-drug interaction is determined to be "additive" or "indifferent" if both active components behave independently of each other respectively have a similar joint action. The term "antagonism" is reserved for cases where a negative impact of the applied active compounds on each other can be seen, basically where they counteract each other. Finally "synergy" is used for cases where the dose-response is significantly potentiated above the intrinsic level of each individual drug alone (J. M. T. Hamilton-Miller, J. Antimicrob. Chemother., 1985, 15, 655-657; G. M. Eliopoulos, R. C. Moellering Jr., "*Antibiotics in laboratory medicine*", 1991, 3$^{rd}$ Ed., The William & Wilkins Co., 432-492).

The drug-drug interaction especially of antibiotics can be assessed at different clinical and preclinical stages. Currently the most widely used in vitro methods to study antibiotic combinations are the checkerboard technique leading to a fractional inhibitory concentration index and the killing curve method (H. O. Hallender et al., *Antimicrob. Agents Chemother.*, 1982; 22, 743-752; M. J. Hall et al., J. Antimicrob. Chemother., 1983, 11, 427-433). Supplemented with a few techniques applying basically the same principles (e.g. R. C. Li et al., *Antimicrob. Agents Chemother.*, 1993; 37, 523-531; Chr. C. Sanders et al., *Antimicrob. Agents Chemother.*, 1993; 37, 260-264) the intention of these tests is primarily the identification of potential synergistic combinations for clinical application or to avoid the use of antagonistic combinations in clinical practice. However, all the in vitro techniques are hampered so far by the deficiency of standardization and especially of a lack of predictive power for the in vivo situation. Therefore in vivo experiments directly assessing the efficacy of the co-administered pharmaceutical compounds are strongly advised.

In the case of tigecycline, combinations with a large array of other antibacterials have been investigated against a wide range of susceptible and multiresistant Gram-positive and Gram-negative bacteria (review: J. M. Entenza, P. Morreillon, *Int. J. Antimicrob. Agents*, 2009, 34, 8.e1-8.e9). In vitro the majority of combinations produce primarily an indifferent response, i.e. neither synergy nor antagonism is observed.

Nevertheless only a few combinations show synergy for some isolates of specific bacteria.

Still there is an increasing need to complement the current arsenal to fight difficult to treat pathogens with a favourable risk-benefit ratio for the patient. Drug combinations offering strong synergistic effects in vivo would therefor provide a major step forward.

The present invention provides a novel combination comprising a β-hairpin peptidomimetic of the formula (I)
cyclo(-Thr-Trp-Ile-Dab-Orn-$^D$Dab-Dab-Trp-Dab-Dab-Ala-Ser-$^D$Pro-Pro), wherein
Dab is (S)-2,4-diaminobutanoic acid;
$^D$Dab is (R)-2,4-diaminobutanoic acid;
Orn is (S)-2,5-diaminopentanoic acid;
all other amino acid residues are L-amino acid residues, if not explicitly designated as D-amino acid residues, following standard IUPAC nomenclature,
and
a compound of the glycylcycline class, especially tigecycline,
or pharmaceutically acceptable salts, or hydrates or solvates thereof.

For avoidance of doubt, hereinafter follows a list of abbreviations, corresponding to generally adopted usual practice, of amino acids which, or the residues of which, are suitable for the purposes of the present invention and referred to in this document.

The descriptors L respectively D, e.g. in $^D$Pro, refer to the stereochemistry at the α-position of the α-amino acid and are used according the Fischer-Rosanoff convention of the IUPAC.

| | | |
|---|---|---|
| Ala | L-Alanine | (S)-2-aminopropanoic acid |
| Ile | L-Isoleucine | (2S,3S)-2-amino-3-methylpentanoic acid |
| Orn | L-Ornithine | (S)-2,5-diaminopentanoic acid |
| Pro | L-Proline | (S)-2-pyrrolidinecarboxylic acid |
| $^D$Pro | D-Proline | (R)-2-pyrrolidinecarboxylic acid |
| Ser | L-Serine | (S)-2-amino-3-hydroxypropanoic acid |
| Thr | L-Threonine | (2S,3R)-2-amino-3-hydroxybutanoic acid |
| Trp | L-Tryptophan | (S)-2-Amino-3-(1H-indol-3-yl)propanoic acid |
| Dab | | (S)-2,4-diaminobutanoic acid |
| $^D$Dab | | (R)-2,4-diaminobutanoic acid; |

In another embodiment this invention provides a combination of compounds that enable therapeutic control of specific bacterial infections in human or animals at doses of the β-hairpin peptidomimetic of the formula (I) lower than the same compound administered alone.

The combination of compounds of the invention can be used in a wide range of applications in order to inhibit the growth of or to kill microorganisms leading to the desired therapeutic effect in man or, due to their similar etiology, in other vertebrates. In particular the claimed combination can be used to inhibit the growth of or to kill microorganisms of a large panel of aerobic or anaerobic, Gram-positive or Gram-negative bacteria, or atypical organisms, but especially vancomycin-resistant enterococci, methicillin-resistant *Staphylococcus aureus*, penicillin-resistant *Streptococcus pneumoniae* and as well as *Pseudomonas aeruginosa*.

When used to treat or prevent infections or diseases related to such infections, particularly nosocomial infections related to diseases such as ventilator-associated pneumonia (VAP), hospital-acquired pneumonia (HAP), healthcare-associated pneumonia (HCAP); catheter-related and non-catheter-related infections such as urinary tract infections (UTIs); related to respiratory diseases such as pneumonia, cystic fibrosis, emphysema and asthma; infections related to skin or soft tissue diseases such as surgical wounds, traumatic wounds and burn wounds; infections related to eye diseases such as keratitis and endophthalmitis; infections related to ear diseases such as otitis; infections related to CNS diseases such as brain abscess and meningitis; infections related to bone diseases such as osteochondritis and osteomyelitis; infections related to cardiovascular diseases such as endocartitis and pericarditis; blood stream infections (BSIs) such as septicemia; infections related to genitourinal diseases such as epididymitis, prostatitis and urethritis; infections related to gastrointestinal diseases such as epidemic diarrhea, necrotizing enterocolitis, typhlitis, gastroenteritis or pancreatitis; or intra-abdominal infections such as bacterial peritonitis; the compounds or respectively their pharmaceutical compositions as the components of the combination of the invention can be administered simultaneously as a single or separate physical entity as well as sequentially, i.e. with a certain time-shift according to dosage regime.

Therefore it is explicitly understood that these components act as a functional unity in a synergistic manner forming a specific embodiment of the invention as a "kit-of-parts".

Pharmaceutical compositions comprising the compounds of the invention, individually or in combination, may be manufactured by means of conventional mixing, dissolving, granulating, coated tablet-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active ingredients into preparations which can be used pharmaceutically. Proper formulation depends upon the method of administration chosen.

For topical administration the pharmaceutically active compounds of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injections, the compounds of the invention may be formulated in adequate solutions, preferably in physiologically compatible buffers such as Hink's solution, Ringer's solution, or physiological saline buffer. The solution may contain formulatory agents such as suspending, stabilizing and/or dispersing agents. Alternatively, the active pharmaceutical ingredients of the invention may be in powder form for combination with a suitable vehicle, e.g. sterile pyrogen-free water, before use.

For transmucosal administration, penetrants appropriate to the barrier to be permeated are used in the formulation as known in the art.

For oral administration, the compounds of the invention can be readily formulated by combining with pharmaceutically acceptable carriers well-known in the art. Such carriers enable the compounds of the invention to be formulated as tablets, pills, dragees, capsules, liquids, gels, syrups, slurries, suspensions etc., for oral ingestion of a patient to be treated. For oral formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP); granulating agents; and binding agents. If desired, disintegrating agents may be added, such as cross-linked polyvinylpyrrolidones, agar, or alginic acid or a salt thereof, such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. In addition, flavoring agents, preservatives, coloring agents and the like may be added.

For buccal administration, the composition may take the form of tablets, lozenges, etc. formulated as usual.

For administration by inhalation, the compounds of the invention can conveniently be delivered in form of an aerosol spray from pressurized packs or a nebulizer, with the use of a suitable propellant, e.g. dichlorodifluoromethane, trichlorofluoromethane, carbon dioxide or another suitable gas. In the case of a pressurized aerosol the dose unit may be determined by providing a valve to deliver a metered amount. Capsules and cartridges of e.g. gelatin for use in an inhaler or insufflator may be formulated containing a powder mix of the compounds of the invention and a suitable powder base such as lactose or starch.

The compounds may also be formulated in rectal or vaginal compositions such as solutions for enema or suppositories together with appropriate suppository bases such as cocoa butter or other glycerides.

In addition to the formulations described previously, the compounds of the invention may also be formulated as depot preparations. Such long acting formulations may be administered by implantation (e.g. subcutaneously or intramuscularly) or by intramuscular injection. For the manufacture of such depot preparations the compounds of the invention may be formulated with suitable polymeric or hydrophobic materials (e.g. as an emulsion in an acceptable oil) or ion exchange resins, or as sparingly soluble salts.

In addition, other pharmaceutical delivery systems may be employed such as liposomes and emulsions well-known in the art. Certain organic solvents such as dimethylsulfoxide may also be employed. Additionally, the pharmaceutically active compounds of the invention may be delivered using a sustained-release system, such as semipermeable matrices of solid polymers containing the therapeutic agent. Various sustained-release materials have been established and are well known by those skilled in the art. Sustained-release capsules may, depending on their chemical nature, release the compounds for a few days up to over 3 years. Depending on the chemical nature and the biological stability of the therapeutic agent, additional strategies analog to protein stabilization may be employed.

As the β-hairpin peptidomimetic as well as the compounds of the glycylcycline class of the invention contain charged residues, respectively may contain charged substructures, they may be, independently, included in any of the above-described formulations as such or as pharmaceutically acceptable salts. Pharmaceutically acceptable salts tend to be more soluble in aqueous and other protic solvents than are the corresponding free base forms.

In addition, the compounds of the present invention and their pharmaceutical acceptable salts may be used per se or in any appropriate formulation in morphological different solid state forms, which may or may not contain different amounts of solvent, e.g. hydrate remaining from the crystallization process.

The β-hairpin peptidomimetic as well as the compounds of the glycylcycline class of the invention, or compositions thereof, will generally be used in an amount effective to achieve the intended purpose. It is to be understood that the amount used will depend on a particular application.

For use to treat or prevent microbial infections or diseases related to such infections, the compounds of the invention, or compositions thereof, are administered or applied in a therapeutically effective amount. By therapeutically effective amount is meant an amount effective in ameliorating the symptoms of, or in ameliorating, treating or preventing microbial infections or diseases related thereto. Determination of a therapeutically effective amount is well within the capacities of those skilled in the art.

For systemic administration, a therapeutically effective dose can be estimated initially from in vitro assays. For example, a dose can be formulated in animal models to achieve a circulating active pharmaceutical ingredient concentration range that includes the $IC_{50}$ as determined in the cell culture (i.e. the concentration of a test compound that is lethal to 50% of a cell culture), the MIC, as determined in cell culture (i.e. the concentration of a test compound that prevents visible growth of a microorganism). Initial dosages can also be determined from in vivo data, e.g. animal models, using techniques that are well known in the art, e.g. as described below in the example part. One having ordinary skills in the art could readily optimize administration to humans based on animal data.

The effective dosage of the active ingredients employed may vary depending on the particular compound or pharmaceutical preparation employed, the mode of administration and the severity and type of the condition treated. Thus, the dosage regimen is selected in accordance with factors including the route of administration and the clearance pathway, e.g. the renal and hepatic function of the patient. A physician, clinician or veterinarian skilled in the art can readily determine and prescribe the amount of the single active ingredient or combination thereof required to prevent, ameliorate or arrest the progress of the condition or disease. Optimal precision in achieving concentration of active ingredients without toxicity requires a regimen based on the kinetics of the active ingredients' availability to the target sites. This involves a consideration of the distribution, equilibrium, and elimination of the active ingredients.

In cases of local administration or selective uptake, the effective local concentration of the compounds of the invention may not be related to plasma concentration. One having the skills in the art will be able to optimize therapeutically effective local dosages without undue experimentation.

Further parameters determining the efficacy, dose, dose regimen and general therapeutic index as a medicament in a clinical setting for the combination or as well for the individual compounds of the invention can be pre-assessed by various in vitro assays. Some of these key parameters are e.g. the minimal bactericidal concentration, minimal inhibitory concentration, antibacterial killing curves, cytotoxicity, hemolysis, plasma stability respectively plasma half-life, microsomal stability, drug metabolism (including drug-drug interaction), protein binding, membrane permeability, solubility etc.

The invention will now be further described in the Examples below, which are intended as an illustration only and not to be construed as limiting the scope of the invention in any way.

EXAMPLES

In Vivo Efficacy Test
Efficacy in Murine Pneumonia Model Against *Pseudomonas aeruginosa* PAX11045 and Estimation of $ED_{50}$
Reference 1:
The efficacy and $ED_{50}$ of the compound of formula (I) ("compound 1") was determined against *Pseudomonas aeruginosa* clinical isolate PAX11045 in a pneumonia model in mice. Colony counts in lung and spleen were determined at 20 hours post treatment.

Infection of Mice
Fresh overnight colonies of PAX11045 from a 5% Horse Blood Agar plate were suspended in 0.9% sterile saline to approximately $10^8$ CFU/ml and further diluted to approximately $5 \times 10^7$ CFU/ml. Female mice (DBA/2, outbred, 18-22 g, Charles River) were anesthetized with 0.08 ml of Zoletil (tiletamine+zolazepam) and inoculated via the nose with a pipette with 0.05 ml of the bacteria suspension containing approximately $10^6$ CFU. 4 hours after inoculation, the mice were treated orally with 45 μl neurophen (20 mg ibuprofen/ml corresponding to approximately 30 mg/kg) as pain relief.

Treatment of Mice with Compound 1
Two vials containing 10 mg of active compound 1 were dissolved in 2.25 ml 0.9% sterile saline each to a concentration of 4.5 mg/ml. One vial was further 2-fold diluted with saline to 2.25, 1.125, 0.56 and 0.28 mg/ml. The mice were treated subcutaneously with 0.2 ml in the neck region with a single dose at 4 hours post infection with a dose calculation based on a mean animal weight of 20 g. As positive control Ciprofloxacin was used in the same manner with a fixed dose of 19 mg/kg.

Sampling
Colony counts were determined post inoculation at 4 hours (untreated mice) and 24 hours (treated and vehicle-only treated mice). Immediately after the mice were sacrificed, the lungs and spleens were collected and frozen at −20° C. After thawing, the organs were homogenized in 1 ml 0.9% saline. Each sample was then 10-fold diluted in saline and 20 μl spots were applied on blood agar plates. All agar plates were incubated 18-48 hours at 35° C. in ambient air.

CFU Counts
The CFU/ml in the inoculum was determined to 7.92 $\log_{10}$ CFU/ml corresponding to 6.62 $\log_{10}$ CFU/mouse.

At 4 hours after infection the mean $\log_{10}$ CFU/lung was 5.28 and the CFU level remained at a similar level after 24 hours in the vehicle-only group. Analog baseline data were collected for the spleen with a mean $\log_{10}$ CFU/spleen of 1.96 at 4 hours, which increased to 2.60 after 24 hours in the vehicle-only group.

Treatment with compound 1 resulted in both organs in a concentration dependent significant reduction of the CFU levels compared to vehicle treatment (p<0.001 for the higher concentrations). Also Ciprofloxacin (19 mg/kg) had a potent effect on reducing the bacterial loads (p<0.001).

Evaluation of the dose-response curve for $ED_{50}$ of compound 1 against PAX11045 in murine lungs using a sigmoidal dose-response model (variable slope) revealed an estimation of 4.33 mg/kg. Table 1 below summarizes the relevant efficacy values.

EXAMPLE 1

The efficacy and $ED_{50}$ of the compound of formula (I) ("compound 1") in combination with tigecycline was determined against *Pseudomonas aeruginosa* clinical isolate PAX11045 in a pneumonia model in mice. Colony counts in lung were determined at 20 hours post treatment.

Infection of Mice
Fresh overnight colonies of PAX11045 from a 5% Horse Blood Agar plate were suspended in 0.9% sterile saline to approximately $10^8$ CFU/ml and further diluted to approximately $5 \times 10^7$ CFU/ml. Female mice (DBA/2, outbred, 18-22 g, Chales River) were anesthetized with 0.08 ml of Zoletil and inoculated via the nose with a pipette with 0.1 ml of the bacteria suspension containing approximately $10^6$ CFU. 4 hours after inoculation, the mice were treated orally with 45 μl neurophen (20 mg ibuprofen/ml corresponding to approximately 30 mg/kg) as pain relief.

Treatment of Mice with Tigecycline 53 mg of tigecycline (Tygacil, Wyeth) was dissolved in 5.3 ml 0.9% sterile saline to a concentration of 10 mg/ml and further diluted with saline to 1.25 mg/ml. The mice were treated subcutaneously with 0.2 ml in the neck region with a single dose at 3 hours post infection corresponding to 12.5 mg/kg on the basis of a mean animal weight of 20 g.

Treatment of Mice with Compound 1

Two vials containing 5 mg of active compound 1 were dissolved in 2.5 ml 0.9% sterile saline each to a concentration of 2 mg/ml. One vial was further 2-fold diluted with saline to 1.1, 0.55, 0.275 and 0.137 mg/ml. The mice were treated subcutaneously with 0.2 ml in the neck region with a single dose at 4 hours post infection with a dose calculation based on a mean animal weight of 20 g. As positive control Ciprofloxacin was used in the same manner with a fixed dose of 20 mg/kg.

Sampling

Colony counts were determined post inoculation at 4 hours (untreated mice) and 24 hours (treated and vehicle-only treated mice). Immediately after the mice were sacrificed, the lungs were collected and frozen at −20° C. After thawing, the organs were homogenized in 1 ml 0.9% saline. Each sample was then 10 fold diluted in saline and 20 μl spots were applied on blood agar plates. All agar plates were incubated 18-24 hours at 35° C. in ambient air.

CFU Counts

The CFU/ml in the inoculum was determined to 7.6 $\log_{10}$ CFU/ml corresponding to 6.3 $\log_{10}$ CFU/mouse.

At 4 hours after infection the mean $\log_{10}$ CFU/lung was 6.13 and the CFU level remained at a similar level after 24 hours in the vehicle-only group.

Treatment with a combination of compound 1 and tigecycline resulted in a concentration dependent significant reduction of the CFU levels compared to vehicle treatment ($p<0.001$). Also Ciprofloxacin (20 mg/kg) had a potent effect on reducing the bacterial loads ($p<0.001$).

Treatment with tigecycline (12.5 mg/kg) alone had no effect on the bacterial loads.

Evaluation of the dose-response curve for $ED_{50}$ of compound 1 in presence of a fixed dose of tigecycline (12.5 mg/kg) against PAX11045 in murine lungs using a sigmoidal dose-response model (variable slope) revealed an estimation of 1.33 mg/kg. The following table summarizes the relevant efficacy values.

TABLE 1

Efficacy values of compound 1

| | compound 1 | compound 1 in presence of 12.5 mg/kg tigecycline |
|---|---|---|
| Top level | 1.3 $\log_{10}$ CFU/ml | 0.13 $\log_{10}$ CFU/ml |
| Bottom level | −2.2 $\log_{10}$ CFU/ml | −2.37 $\log_{10}$ CFU/ml |
| $E_{max}$ | 3.5 $\log_{10}$ CFU/ml | 2.5 $\log_{10}$ CFU/ml |
| $ED_{50}$ | 4.33 mg/kg | 1.33 mg/kg |
| Static dose | 1.55 mg/kg | 0.74 mg/kg |
| 1 log killing dose | 8.1 mg/kg | 1.2 mg/kg |
| 2 log killing dose | 20 mg/kg | 2.1 mg/kg |
| $R^2$ | 0.55-0.75 | 0.77 |

The invention claimed is:

1. A combination comprising:
   a β-hairpin peptidomimetic of the formula cyclo(-Thr-Trp-Ile-Dab-Orn-DDab-Dab-Trp-Dab-Dab-Ala-Ser-DPro-Pro) (I), wherein Dab is (S)-2,4-diaminobutanoic acid, DDab is (R)-2,4-diaminobutanoic acid, and Orn is (S)-2,5-diaminopentanoic acid; and
   a compound of the glycylcycline class,
   or pharmaceutically acceptable salts.

2. A combination according to claim 1 wherein the compound of the glycylcycline class is tigecycline or a pharmaceutically acceptable salt thereof.

3. A pharmaceutical composition comprising a combination according to claim 1 and at least one pharmaceutically inert carrier.

4. A pharmaceutical composition according to claim 3 in a form suitable for oral, topical, transdermal, injection, infusion, buccal, transmucosal, rectal, vaginal, pulmonary or inhalation administration, especially in the form of tablets, dragees, capsules, solutions, liquids, gels, plaster, creams, ointments, syrup, slurries, powders, suspensions, spray, nebulizer or suppositories.

5. A kit comprising a part containing a β-hairpin peptidomimetic of the formula (I) according to claim 1, or a pharmaceutically acceptable salt thereof and a part containing a compound of the glycylcycline class or a pharmaceutically acceptable salt thereof.

6. A kit according to claim 5 wherein the compound of the glycylcycline class is tigecycline or a pharmaceutically acceptable salt thereof.

7. A method of treating a bacterial infection or disease related to such infection in human or animals comprising administering to a subject in need thereof an adequate amount of a combination according to claim 1.

8. A method of treating a bacterial infection or disease related to such infection in human or animals comprising a kit according to claim 5.

9. A method of manufacturing a pharmaceutical composition comprising the step of combining the combination according to claim 1 with at least one pharmaceutically inert carrier.

10. A method of treating a bacterial infection or disease related to such infection in human or animals comprising administering to a subject in need thereof a therapeutically acceptable amount of a pharmaceutical composition according to claim 3.

* * * * *